United States Patent
Bhamidipati et al.

(10) Patent No.: US 10,663,448 B2
(45) Date of Patent: May 26, 2020

(54) METHODS OF RANKING FORMATION STABILIZER PERFORMANCE

(71) Applicant: HALLIBURTON ENERGY SERVICES, INC., Houston, TX (US)

(72) Inventors: Venkata Satya Srikalyan Bhamidipati, Kingwood, TX (US); Ajish Potty, Stafford, TX (US); Syed Muhammad Farrukh Hamza, Houston, TX (US)

(73) Assignee: HALLIBURTON ENERGY SERVICES, INC., Houston, TX (US)

(*) Notice: Subject to any disclaimer, the term of this patent is extended or adjusted under 35 U.S.C. 154(b) by 0 days.

(21) Appl. No.: 15/505,650

(22) PCT Filed: Nov. 6, 2014

(86) PCT No.: PCT/US2014/064348
§ 371 (c)(1),
(2) Date: Feb. 22, 2017

(87) PCT Pub. No.: WO2016/072994
PCT Pub. Date: May 12, 2016

(65) Prior Publication Data
US 2017/0241972 A1    Aug. 24, 2017

(51) Int. Cl.
*E21B 21/06* (2006.01)
*G01N 33/24* (2006.01)
*E21B 49/00* (2006.01)
*G01N 21/51* (2006.01)
*G01N 21/64* (2006.01)

(52) U.S. Cl.
CPC ........... *G01N 33/24* (2013.01); *E21B 21/062* (2013.01); *E21B 49/005* (2013.01); *G01N 21/51* (2013.01); *G01N 21/64* (2013.01); *G01N 33/241* (2013.01)

(58) Field of Classification Search
CPC .......................... E21B 21/062; E21B 49/005
USPC .................................................... 166/305.1
See application file for complete search history.

(56) References Cited

U.S. PATENT DOCUMENTS

| | | | |
|---|---|---|---|
| 1,049,873 A | 1/1913 | Kopke | |
| 2,761,837 A | 9/1956 | Brown et al. | |
| 3,851,976 A | 12/1974 | Meier | |
| 4,158,521 A * | 6/1979 | Anderson | C09K 17/18 166/295 |

(Continued)

FOREIGN PATENT DOCUMENTS

CN    101585775 A    11/2009

OTHER PUBLICATIONS

El-Shall et al. "Mechanisms of Grinding Modification by Chemical Additives: Organic Reagents," Powder Technology, 1984, pp. 267-273, 38.

(Continued)

*Primary Examiner* — Zakiya W Bates
*Assistant Examiner* — Ashish K Varma
(74) *Attorney, Agent, or Firm* — Haynes and Boone, LLP

(57) ABSTRACT

Methods of ranking formation stabilizer performance are described. The methods include obtaining drill cuttings from a subterranean formation, grinding and sieving the drill cuttings to a particle size larger than 200 mesh, adding a formation stabilizer solution to the ground and sieved drill cuttings to form a mixture, agitating the mixture, and measuring turbidity of the agitated mixture.

20 Claims, 2 Drawing Sheets

(56) References Cited

U.S. PATENT DOCUMENTS

| | | | | |
|---|---|---|---|---|
| 4,599,117 A | * | 7/1986 | Luxemburg | B01D 37/02 |
| | | | | 134/25.1 |
| 7,538,880 B2 | | 5/2009 | Moore et al. | |
| 8,281,859 B2 | * | 10/2012 | Roddy | C04B 18/162 |
| | | | | 106/751 |
| 9,518,463 B2 | * | 12/2016 | Hedges | E21B 21/003 |
| | | | | 175/58 |
| 2003/0116887 A1 | * | 6/2003 | Scott | C04B 18/049 |
| | | | | 264/333 |
| 2012/0178651 A1 | | 7/2012 | Huang | |

OTHER PUBLICATIONS

Fink, Johannes, "Petroleum Engineer's Guide to Oil Field Chemicals and Fluids", 2012, pp. 125-148, Gulf Professional Publishing, Oxford, UK.

International Search Report and Written Opinion for International Application No. PCT/US2014/060919 dated Jul. 29, 2015. (8 pages).

* cited by examiner

METHODS OF RANKING FORMATION STABILIZER PERFORMANCE

CROSS-REFERENCE TO RELATED APPLICATION

The present application is a U.S. National Stage patent application of International Patent Application No. PCT/US2014/064348, filed on Nov. 6, 2014, the benedift of which is claimed and the disclosure of which is incorporated herein by reference in its entirety.

BACKGROUND

The present invention relates generally to methods of ranking various formation stabilization treatments based on their ability to minimize formation damage using turbidity measurements of formation cuttings in different formation stabilizer solutions.

Maintaining wellbore stability is an important issue in the oil and gas industry. When a well is drilled, the formation around the wellbore must sustain the load that was previously taken by the removed formation. As a result, an increase in stress around the wellbore is produced. Wellbore stability is not only a mechanical problem. The interaction of chemicals in the treatment fluid with the formation also influences wellbore stability. There are various chemicals in the treatment fluid that can physically and chemically interact with the formations.

For example, formations containing clays are prone to water-sensitivity, which can cause damage to the formation through swelling, softening, and/or generation of migrating fines. The stability of the fracture-face of a formation depends on the sensitivity of the formation to water and other oilfield fluid components such as those used in fracturing. Fracture-face instability can result in proppant embedment, fines release, delamination, and extrusion. All of these can significantly reduce fracture permeability and decrease oil production.

Clays in the formation can swell, disperse, disintegrate or otherwise become disrupted in the presence of aqueous fluids. The swelling or dispersion of clays can significantly reduce the permeability of a formation and reduce mechanical strength of the formation. Some clays, in the presence of aqueous solutions, will expand and be disrupted to the extent that they become unconsolidated and produce particles that migrate into pore throats in the formation/proppant packs and reduce permeability/conductivity of the formation/fracture. In addition, many shales and/or clays are reactive with fresh water, resulting in ion exchange and absorption of aqueous fluids leading to loss of hardness of the rock in the formation.

Current approaches to determining formation stability involve examining rock mechanical properties using tests like the Quad cell embedment test or the Brinell hardness test to determine the best formation stabilizer to use in a formation. These traditional tests, however, require capital-intensive equipment, well-trained lab personnel, and core samples from each well at different depths. Obtaining core samples for each well and each zone of interest is typically very difficult. This problem is exacerbated by clay-rich layers being unstable for good core samples.

Typically formation stabilizers like inorganic salts and other cationic molecules are used to mitigate damage of water-sensitive formations caused due to the interaction of clays and/or other formation materials with aqueous fluids. However, there are no methods to efficiently and quickly determine the performance of formation stabilizers. Moreover, shales are highly heterogeneous formations which require specific formation stabilizers depending on the formation mineralogy.

Thus, there is a continuing need for improved methods for determining an optimum formation stabilizer for use in subterranean formations.

BRIEF DESCRIPTION OF THE DRAWINGS

The following figures are included to illustrate certain aspects of the present invention, and should not be viewed as an exclusive embodiment. The subject matter disclosed is capable of considerable modification, alteration, and equivalents in form and function, as will occur to those skilled in the art and having the benefit of this disclosure.

DETAILED DESCRIPTION

Figure 1:
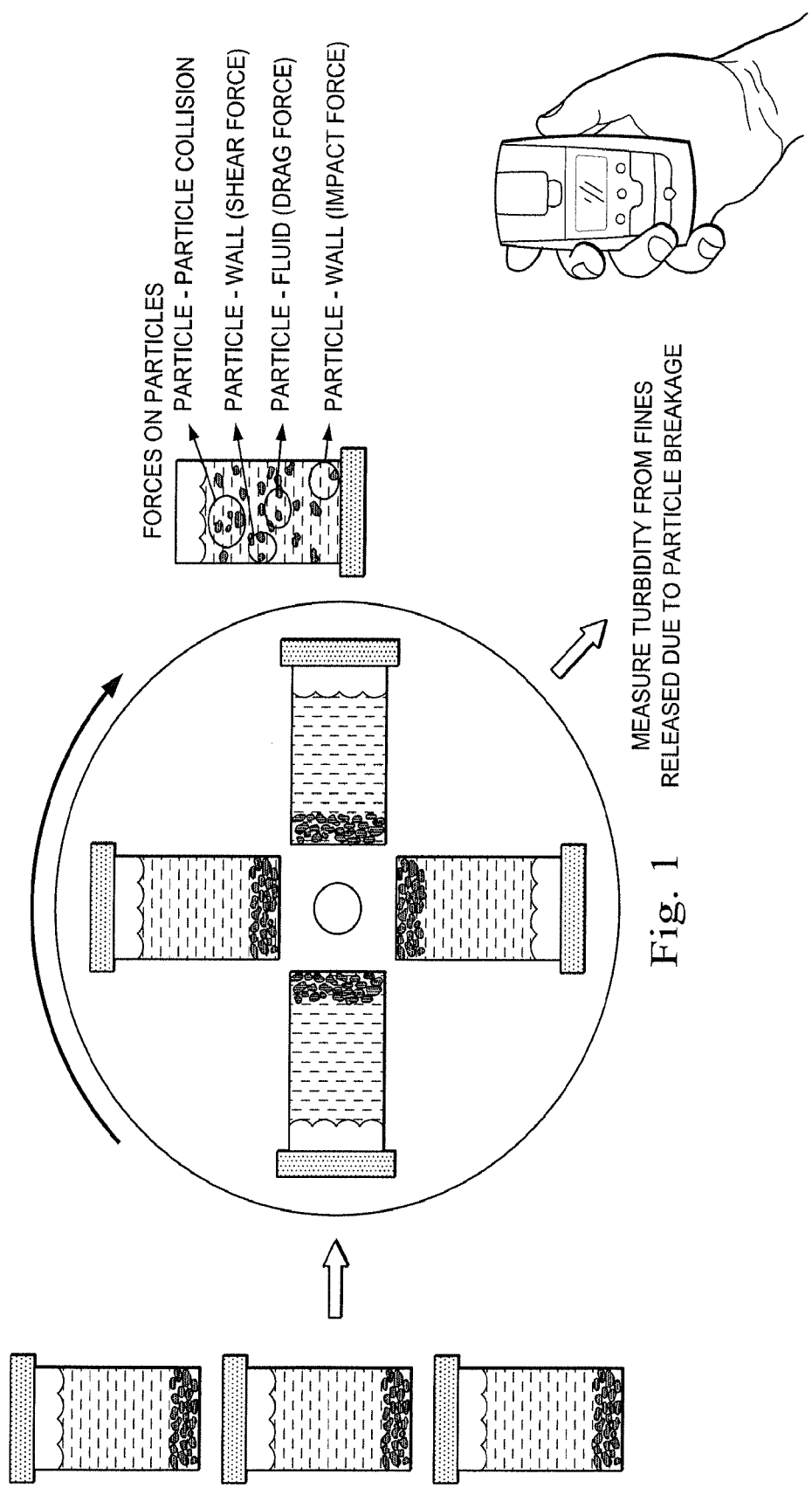
FIG. 1 shows an exemplary turbidity test and the forces acting on particles during end-over-end rotation according to embodiments of the present invention.

According to several exemplary embodiments, methods are provided for ranking various formation stabilizers based on their ability to minimize formation damage using turbidity measurements. By "turbidity" is meant a measure of the cloudiness of a fluid caused by particles that are dissolved or suspended in the fluid. The particles may or may not be visible to the naked eye. The more total suspended solids in the fluid, the cloudier it appears and the higher the turbidity.

The methods use turbidity measurements to quantify the effect of formation stabilizers, e.g., clay stabilizers, on rock properties and provide estimates of formation stability (combination rock mechanical and chemical properties) in the presence of formation stabilizers, and in some embodiments, other additives in the fluid. According to several exemplary embodiments, the methods measure fines released (or turbidity) from mechanical agitation of drill cuttings in different formation stabilizers.

Advantageously, the methods determine rock stability using drill cuttings instead of core samples of the formation. Drilling cuttings are produced as the rock is broken by a drill bit advancing through the rock. The cuttings are usually carried to the surface by drilling fluid circulating up from the drill bit. Drill cuttings are then separated from the drilling fluid by shale shakers and other wellsite equipment.

According to several exemplary embodiments, the drill cuttings are ground and sieved. For example, the drill cuttings can be ground and sieved to a particle size larger than US 200 mesh. In another example, the ground and sieved drill cuttings have a particle size larger than US 100 mesh. In several examples, the drill cuttings have a particle size larger than US 40 mesh. In yet another example, the ground and sieved drill cuttings have a particle size larger than about US 30-40 mesh.

According to several exemplary embodiments, the methods allow usage of a simple field lab test using drill cuttings to obtain formation stability (relative to fluid without any formation stabilizer treatment) of the rock in the presence of given treatment fluids. Turbidity is used as a proxy to quantify the effect of chemicals on rock properties. The test results recommend the optimum formation stabilizer for a given formation to be included in the stimulation treatment design.

According to several exemplary embodiments, the methods are field-lab deployable test methods that quantify mechanical and chemical stability of clay-rich rocks treated with various formation stabilizers. Advantageously, the test methods can be implemented in field labs or other locations on-site or off-site without the requirement of heavy, complicated, or expensive equipment. In addition, the test methods are easily implementable, low cost, provide quick analysis, and require no special training. The methods provide optimized formation control treatments based on reservoir characteristics.

According to several exemplary embodiments, methods of ranking formation stabilizer performance include obtaining drill cuttings from a subterranean formation, grinding and sieving the drill cuttings to a particle size larger than 200 mesh, adding a formation stabilizer solution, e.g., an aqueous clay stabilizer solution, to the ground and sieved drill cuttings to form a mixture, agitating the mixture, and measuring turbidity of the agitated mixture.

A lower turbidity indicates a better stabilization of the drill cuttings, and better performance of the formation stabilizer. The more turbid the mixture, the less stable the drill cuttings, and the less compatible the drill cuttings are with the specific formation stabilizer. Also, the more turbid the mixture, the more the drill cuttings have disintegrated, and therefore, the softer the rock. Thus, the testing methods described herein correlate turbidity with both mechanical and chemical stability of the rock.

According to several exemplary embodiments, the agitated mixtures retain a turbid or opalescent appearance characteristic of that caused by the scattering of incident light by suspended colloidal particles. The appearance of such a colloidal condition indicates that the drill cuttings have not been stabilized by the formation stabilizer solution. Obviously, when the drill cuttings swell or disperse they have not been stabilized by the particular formation stabilizer tested.

According to several exemplary embodiments, the subterranean formation includes a clay. Among the clays that may be present originally in the formation, or may have been introduced therein are clay materials of the smectite (montmorillonite) group such as montmorillonite, saponite, nontronite, hectorite, beidellite, and sauconite; the kaolin group such as kaolinite, nacrite, dickite, endellite and halloysite; the illite (hydrous-mica) group such as hydrobiotite, glauconite, and illite; the chlorite group (both 7 and 14 angstrom basal spacings) such as chlorite, greenalite and chamosite; clay minerals not belonging to the above groups such as vermiculite, palygorskite (attapulgite) and sepiolite; and mixed-layer (both regular and irregular) varieties of the above minerals. The clay content of the formations can include a single species of a clay mineral or several species, including the mixed-layer types of clay. The clay-containing formations need not be composed entirely of clay, but may contain other mineral components associated therewith. The clays in the formation may be of varying shapes, such as minute, plate-like, tube-like and/or fiber-like particles having an extremely large surface area.

According to several exemplary embodiments, the clay-containing subterranean formation includes a shale. Shale is a fine-grained, clastic sedimentary rock composed of a mix of clay minerals and fragments of other minerals such as quartz, calcite, pyrite, chlorite, feldspar, opal, cristobalite, biotite, clinoptilite, gypsum, and the like. The ratio of clay to the other minerals may vary depending on the source of the shale. In an embodiment, the clay present in the shale can include a smectite, illite, mixed smectite-illite layer, chlorite, corrensite, kaolinite clay, and/or any combination thereof. As an example, a smectite clay may be sodium bentonite that may contain sodium in addition to the components magnesium, aluminum and silica. Additional species of smectite clay include hectorite, saponite, nontronite, beidellite, and/or sauconite.

According to several exemplary embodiments, the formation stabilizer is any suitable chemical additive that prevents the migration or swelling of formation particles in reaction to a water-based fluid. Examples of formation stabilization products that may be used include, but are not limited to, potassium chloride, sodium chloride, ammonium chloride, tetramethyl ammonium chloride, cationic polymers, cationic surfactants, hydrophobic resins, transition metals, furfuryl alcohols, ethylene glycol, quaternary amines, bisquaternary amines and the like.

Various methods exist for measuring the turbidity of a liquid media. These methods are based on ultrasounds, radioactive materials, or light. Methods based on light are classified into (1) methods that use transmitted light or (2) methods that use scattered light. In the first method, a diminishing signal, which indicates the intensity or amount of transmitted light, denotes an increase in the suspended solid particles present, i.e., the turbidity of the liquid. In the latter method, an increase in the amount of light detected indicates that more particles are present.

Another method uses fluorescence to measure turbidity. For example, one or more fluorescent materials may be added to the mixture. When light is passed through the mixture, the fluorescent material converts part of the light into fluorescent light. The amount of fluorescent light can then be measured. The presence of solid particles (turbidity) in the mixture affects the measurement. The particles can scatter the fluorescent light and increase the quantity of light measured. The particles can also weaken the fluorescent light as a result of scatter and absorption. Thus, the fluorescent light that is measured can serve as an indication of how turbid the mixture is. If the interfering substance is reflective, turbidity can create light scatter and readings will increase. If the interfering substance absorbs light, fluorescence will be reduced.

Instead of optical measurements, turbidity can also be measured acoustically. An acoustic instrument emits an ultrasonic sound pulse and measures the reflections.

Turbidity can be measured using, for example, a handheld turbidity meter. Turbidity is usually measured in nephelometric turbidity units (NTU) or Jackson turbidity units (JTLJ), depending on the method used for measurement.

The following examples are illustrative of the compositions and methods discussed above and are not intended to be limiting.

Example 1

Turbidity Test on Barnett Shale Cuttings

A turbidity test was performed on drill cuttings obtained from the Barnett Shale in Texas. The drill cuttings were ground and sieved through US 30-mesh and US 40-mesh sieves and gently mixed in a given amount of an aqueous formation stabilizer solution. The mixture was then rotated end-over-end for 10 minutes to 120 minutes at 15 rpm, and turbidity measurements were taken using a Hach® Company model 2100P turbidity meter as shown in FIG. 1. The formation stabilizer solutions can be made in deionized water, tap water, produced water, source water, or broken fracturing fluid. In this example, the solutions were made using deionized water.

Figure 2:
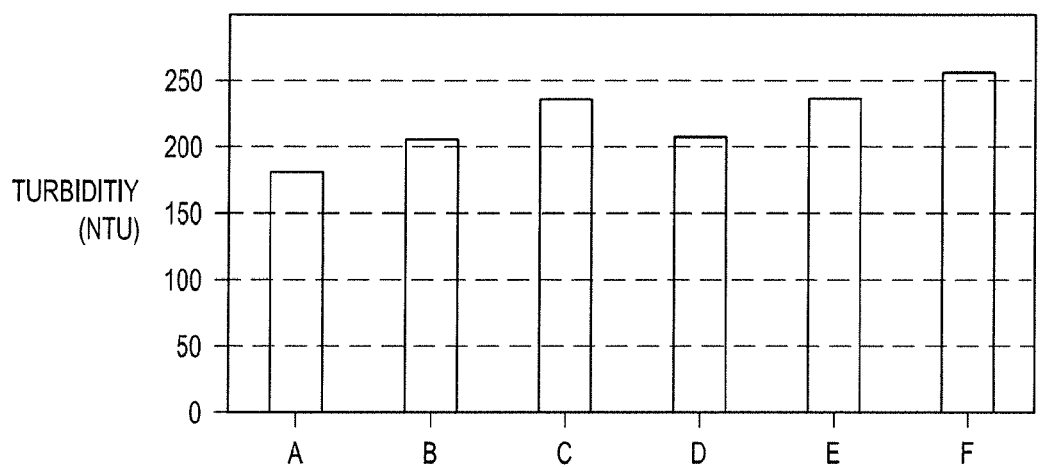
FIG. 2 shows the results of a turbidity test performed on Barnett Shale cuttings for different formation stabilizers according to embodiments of the present invention.

The results of the test are shown in FIG. 2. The different formation stabilizer solutions are denoted with the letters A-F. Solution A contains one gram per ton (gpt) of Cla-Sta® FS additive; Solution B contains 1 gpt of Cla-Web℠ additive; Solution C contains 1 gpt of Cla-Sta® XP additive; Solution D contains 10 gpt Clayfix 3™ additive; Solution E contains 7% by weight potassium chloride (KCl); and Solution F is water. The formation stabilizers in Solutions A-D are marketed by Halliburton Energy Services, Inc.

As can be seen, Solution A had the lowest turbidity. It therefore offers the best stability for the drill cuttings and the best protection in this example.

The test allows the selection of an optimum formation stabilizing product for a given reservoir and allows useful information regarding rock properties (in the presence of given fluids) to be used by drilling engineers to optimize the drilling process and by fracture engineers to customize a fracture job. It provides a rapid well-site screening method for chemicals and quantifies their impact on rocks.

Example 2

Comparison of Brinell Hardness and Turbidity

Barnett Shale core samples were prepared, and the core sample disks were submerged in the formation stabilizer solutions of Example 1. The samples were left under vacuum for 2 days, and then tested using a Brinell hardness tester using the fixed displacement method. Relative hardness numbers were calculated from the Brinell test data and were compared to relative hardness numbers calculated from turbidity data for the Barnett Shale samples.

Figure 3:
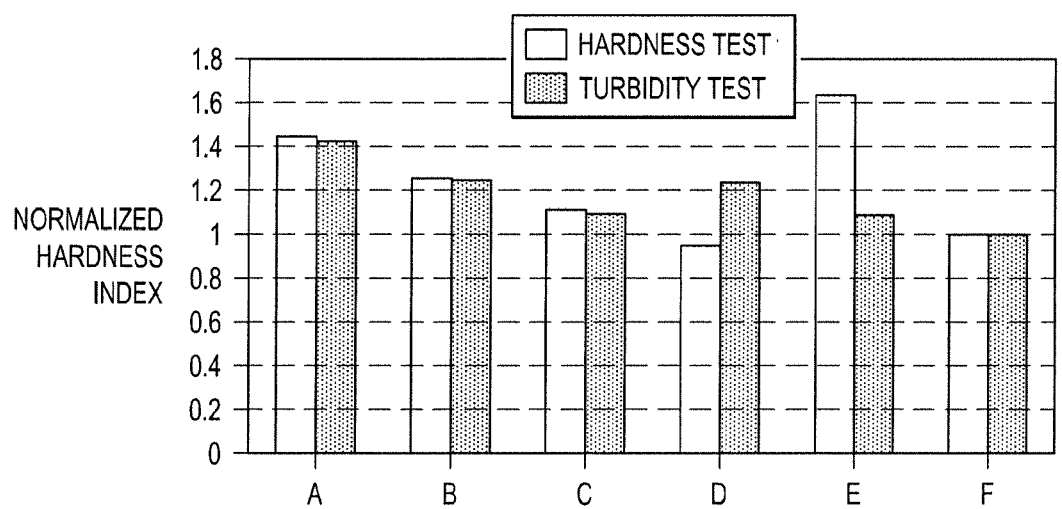
FIG. 3 shows a comparison of relative hardness to water using a turbidity test with drill cuttings and Brinell hardness with core samples of Barnett Shale.

Relative hardness numbers was calculated using the following formula:

Relative Hardness (from Turbidity)=sample turbidity in water/sample turbidity in formation stabilizer solution Relative Hardness (from Brinell Test)=Brinell Hardness of core in formation stabilizer solution/Brinell Hardness of core in water Relative hardness numbers calculated from the turbidity test matched closely with relative hardness calculated using the Brinell hardness tester. As shown in FIG. 3, there was reasonably good correlation of turbidity with Brinell hardness. The turbidity test offers an advancement in testing rock hardness using drill cuttings compared to traditional methods that require core samples. Hardness is one of the proxies considered for mechanical stability. Similarly, other measures such as scratch tests, stiffness, and traditional compressive, shear or tensile strength tests can also be utilized. A large number of these tests performed on a variety of subsurface lithologies provide a basis for a database of mechanical and chemical stability properties, benchmarked against different types of formation stabilizers.

Although only a few exemplary embodiments have been described in detail above, those of ordinary skill in the art will readily appreciate that many other modifications are possible in the exemplary embodiments without materially departing from the novel teachings and advantages of the present invention. Accordingly, all such modifications are intended to be included within the scope of the present invention as defined in the following claims.

What is claimed is:

1. A method comprising:
producing drill cuttings in a drilling fluid as a subterranean formation is drilled with the drilling fluid, wherein the subterranean formation comprises shale;
separating the drill cuttings from the drilling fluid to obtain drill cuttings from the subterranean formation;
grinding and sieving the drill cuttings to a particle size between 420 microns to 595 microns;
adding a formation stabilizer solution to the ground and sieved drill cuttings to form a mixture;
agitating the mixture; and
measuring turbidity of the agitated mixture.

2. The method of claim 1, further comprising deducing a chemical stability, a mechanical stability, or both, of the formation from the turbidity measurement.

3. The method of claim 2, further comprising correlating the turbidity measurement to a rock mechanical stability.

4. The method of claim 3, wherein the rock mechanical stability comprises a hardness, a compressive strength, a tensile strength, a shear strength, a stiffness, or any combination thereof.

5. The method of claim 2, wherein a chemical stability, a mechanical stability, or both are deduced at a planar feature.

6. The method of claim 5, wherein the planar feature comprises a fracture face of the formation.

7. The method of claim 1, performed on-site or off-site.

8. The method of claim 1, wherein the shale comprises clays of the smectite group, the kaolin group, the ilite group, the chlorite group, or any combination thereof.

9. The method of claim 1, wherein agitating the mixture comprises rotating the mixture end-over-end.

10. The method of claim 1, wherein the formation stabilizer solution comprises one or more of potassium chloride, sodium chloride, ammonium chloride, tetramethyl ammonium chloride, a cationic polymer, a cationic surfactant, a hydrophobic resin, a transition metal, a furfuryl alcohol, ethylene glycol, a quaternary amine, or a bisquaternary amine.

11. A method comprising:
producing drill cuttings in a drilling fluid as a subterranean formation is drilled with the drilling fluid, wherein the subterranean formation comprises shale;
separating the drill cuttings from the drilling fluid to obtain drill cuttings from the subterranean formation;
grinding and sieving the drill cuttings to a particle size between 420 microns to 595 microns;
adding a plurality of formation stabilizer solutions to the ground and sieved drill cuttings to form a plurality of mixtures;
agitating the plurality of mixtures; and
measuring turbidity of the plurality of agitated mixtures.

12. The method of claim 11, further comprising comparing the turbidity of the plurality of agitated mixtures and selecting the least turbid mixture.

13. The method of claim 11, further comprising deducing a chemical stability, a mechanical stability, or both, of the formation from the turbidity measurements.

14. The method of claim 11, further comprising correlating the turbidity measurements to a rock hardness.

15. The method of claim 14, wherein the rock hardness comprises a Brinell hardness, a strength or a stiffness.

16. The method of claim 11, wherein a chemical stability, a mechanical stability, or both are deduced at any representative location of drilling cuttings of the formation.

17. The method of claim 11, wherein the formation stabilizer solutions comprise one or more of potassium chloride, sodium chloride, ammonium chloride, tetramethyl ammonium chloride, a cationic polymer, a cationic surfactant, a hydrophobic resin, a transition metal, a furfuryl alcohol, ethylene glycol, a quaternary amine, or a bisquaternary amine.

18. A method of ranking formation stabilizer performance comprising:
  producing drill cuttings in a drilling fluid as a shale formation is drilled with the drilling fluid;
  separating the drill cuttings from the drilling fluid to obtain drill cuttings from the shale formation;
  grinding and sieving the drill cuttings to a particle size between 420 microns to 595 microns;
  adding a plurality of formation stabilizer solutions to the ground and sieved drill cuttings to form a plurality of mixtures;
  rotating the plurality of mixtures end-over-end;
  measuring turbidity of the plurality of agitated mixtures;
  comparing the turbidity of the plurality of agitated mixtures; and
  selecting the least turbid mixture.

19. The method of claim 18, further comprising treating the shale formation with the formation stabilizer solution in the least turbid mixture.

20. The method of claim 18, wherein the formation stabilizer solutions comprise one or more of potassium chloride, sodium chloride, ammonium chloride, tetramethyl ammonium chloride, a cationic polymer, a cationic surfactant, a hydrophobic resin, a transition metal, a furfuryl alcohol, ethylene glycol, a quaternary amine, or a bisquaternary amine.

* * * * *

UNITED STATES PATENT AND TRADEMARK OFFICE
CERTIFICATE OF CORRECTION

PATENT NO. : 10,663,448 B2
APPLICATION NO. : 15/505650
DATED : May 26, 2020
INVENTOR(S) : Venkata Satya Srikalyan Bhamidipati, Ajish Potty and Syed Muhammad Farrukh Hamza Page 1 of 1

It is certified that error appears in the above-identified patent and that said Letters Patent is hereby corrected as shown below:

In the Specification

Column 1, Line 9, change "benedift" to -- benefit --

Signed and Sealed this
Twenty-seventh Day of October, 2020

Andrei Iancu
*Director of the United States Patent and Trademark Office*